United States Patent [19]
Balaban et al.

[11] Patent Number: 5,456,679
[45] Date of Patent: * Oct. 10, 1995

[54] DELIVERY DEVICES WITH PULSATILE EFFECT

[75] Inventors: Stephen M. Balaban, Chesterfield; James B. Pike, St. Peters; Jonathan P. Smith, St. Louis; Clifton A. Baile, Chesterfield, all of Mo.

[73] Assignee: Alza Corporation, Palo Alto, Calif.

[*] Notice: The portion of the term of this patent subsequent to May 3, 2011 has been disclaimed.

[21] Appl. No.: 352,268

[22] Filed: Dec. 7, 1994

Related U.S. Application Data

[63] Continuation of Ser. No. 257,422, Jun. 9, 1994, abandoned, which is a continuation of Ser. No. 133,237, Oct. 5, 1993, abandoned, which is a continuation of Ser. No. 58,151, May 5, 1993, Pat. No. 5,308,348, which is a continuation-in-part of Ser. No. 837,183, Feb. 18, 1992, Pat. No. 5,209,746.

[51] Int. Cl.⁶ ........................................ A61K 9/22
[52] U.S. Cl. ................................ 604/892.1; 604/890.1; 604/143; 424/422
[58] Field of Search ................. 604/19–22, 890.1, 604/891.1, 892.1, 143; 424/422

[56] References Cited

U.S. PATENT DOCUMENTS

| | | | |
|---|---|---|---|
| 3,760,806 | 9/1973 | Leeper | 604/892.1 |
| 4,416,659 | 11/1983 | Simpson et al. | 604/48 |
| 4,507,115 | 3/1985 | Kambarra et al. | 604/891.1 |
| 4,623,958 | 2/1988 | Pope | 604/890.1 |
| 4,642,230 | 2/1987 | Whitehead et al. | 604/890.1 |
| 4,723,958 | 2/1988 | Pope | 604/890.1 |
| 4,777,049 | 10/1988 | Magruder et al. | 424/457 |
| 4,842,867 | 6/1989 | Ayer et al. | 424/473 |
| 4,867,980 | 9/1989 | Edwards et al. | 424/438 |
| 4,874,388 | 10/1989 | Wong et al. | 604/891.1 |
| 4,957,494 | 9/1990 | Wong et al. | 604/892.1 |
| 4,969,873 | 11/1990 | Steinbach | 604/891.1 |
| 4,997,420 | 3/1991 | Lefevre | 604/121 |
| 5,023,088 | 6/1991 | Wong et al. | 424/473 |
| 5,029,746 | 5/1993 | Balaban et al. | 604/890.1 |
| 5,059,175 | 10/1991 | Hanover et al. | 604/890.1 |
| 5,122,128 | 6/1992 | Cordinal et al. | 604/890.1 |
| 5,167,625 | 12/1992 | Jacobsen et al. | 604/890.1 |
| 5,196,002 | 3/1993 | Hanover et al. | 604/891.1 |
| 5,209,746 | 5/1993 | Balaban et al. | 604/890.1 |
| 5,221,278 | 6/1993 | Linkwitz | 604/892.1 |
| 5,227,167 | 7/1993 | Carr et al. | 604/892.1 |
| 5,308,348 | 5/1994 | Balaban et al. | 604/892.1 |

FOREIGN PATENT DOCUMENTS

| | | | |
|---|---|---|---|
| WO8600519 | 1/1986 | WIPO | 604/890.1 |

*Primary Examiner*—C. Fred Rosenbaum
*Assistant Examiner*—Chalin Smith
*Attorney, Agent, or Firm*—Richard T. Ito; Edward L. Mandell; Steven F. Stone

[57] ABSTRACT

Delivery devices which include a beneficial agent and an activating mechanism in separate compartments separated by a moveable partition are designed to deliver the beneficial agent in a pulsatile manner through an orifice. The pulsatile delivery is achieved by a band of resilient material which is placed over the orifice. The resilient material is sufficiently tight to substantially seal the orifice when the pressure within the device is below a threshold level while at the same time being capable of being stretched when the internal pressure exceeds the threshold.

15 Claims, 1 Drawing Sheet

U.S. Patent     Oct. 10, 1995     5,456,679
FIG.1
FIG.2
FIG.3
FIG.4
FIG.5
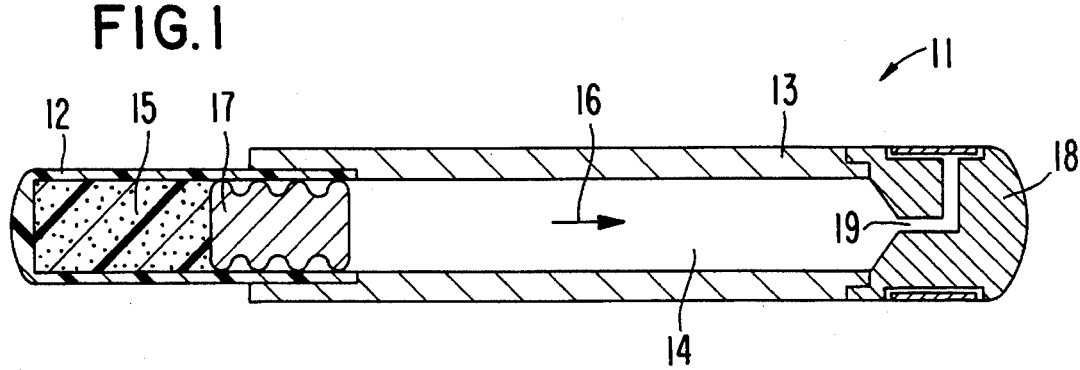
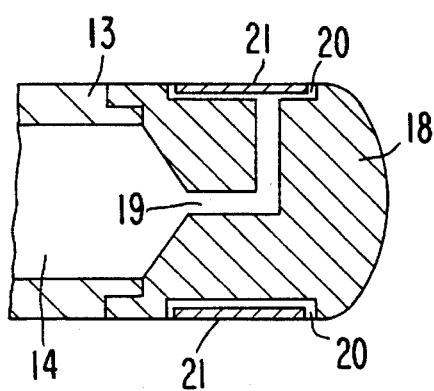
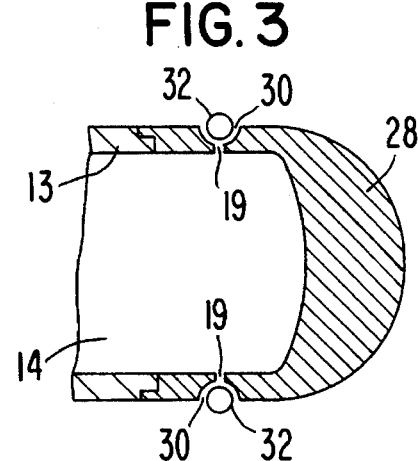
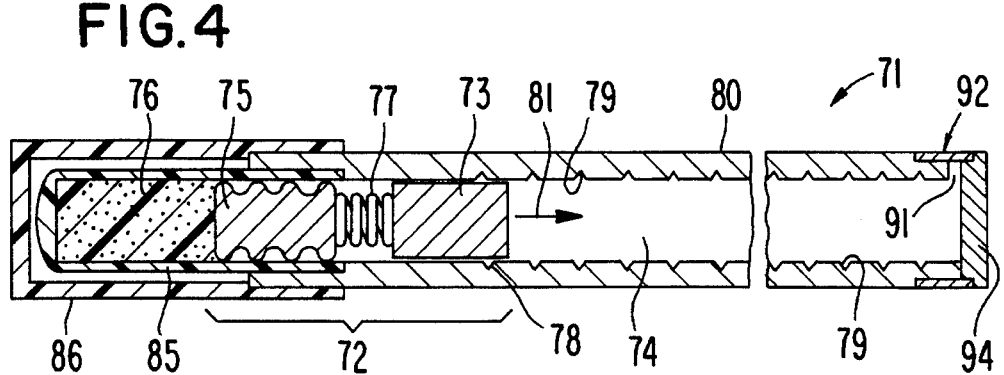
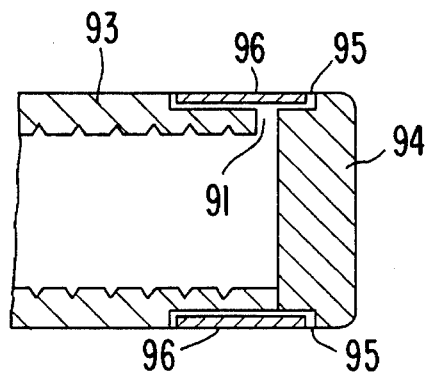

DELIVERY DEVICES WITH PULSATILE EFFECT

RELATED APPLICATIONS

This application is a continuation of application Ser. No. 08/257,422, filed Jun. 9, 1994, now abandoned, which is continuation of application Ser. No. 08/133,237, filed Oct. 5, 1993, now abandoned, which is a continuation of application Ser. No. 08/058,151, filed May 5, 1993, now U.S. Pat. No. 5,308,348, which is continuation-in-part of application Ser. No. 07/837,183, filed Feb. 18, 1992, now U.S. Pat. No. 5,209,746 and benefit of the filing date of said earlier filed applications is claimed under 35 § U.S.C. 120.

FIELD OF THE INVENTION

This invention lies in the field of controlled- or sustained-release systems for the delivery of drugs, nutrients and the like. In particular, this invention relates to delivery systems which are generally in the form of capsules designed to release a beneficial agent through an orifice in the capsule, the release occurring gradually as the result of internal pressure.

BACKGROUND OF THE INVENTION

Osmotic delivery capsules, commonly referred to as "osmotic pumps," function by virtue of walls which selectively pass water into the capsule reservoir. Absorption of water by the capsule through these walls is driven by a water-attracting agent in the capsule interior which creates osmotic pressure across the capsule wall. The water-attracting agent may be the beneficial agent itself whose controlled release is sought, but in most cases, it is a separate agent specifically selected for its ability to draw water, this separate agent being isolated from the beneficial agent at one end of the capsule. In either case, the structure of the capsule wall does not permit the capsule to expand, and as a result, the water uptake causes discharge of the beneficial agent through an orifice in the capsule at the same rate that water enters by osmosis.

The terms "osmotically effective" and "osmotically active" are used in the literature to characterize the water-attracting agent which drives the osmotic flow. Certain agents of this type are termed "osmagents," which denotes water-soluble compounds to which the capsule wall is not permeable. Osmotically effective agents which are polymeric species are termed "osmopolymers," which term denotes water-swellable polymers. Osmagents and osmopolymers may be used individually in a capsule or they may be present as a mixture of the two. In cases where the osmotically active agent is separated from the beneficial agent by a movable partition or piston, the osmotically active agent and the compartment in which it resides may be referred to as an "osmotic engine."

Many protocols or situations require, or would benefit from, an intermittent or pulsatile release of the beneficial agent from the capsule. This is true of a variety of drugs, medicaments and nutriments, in a range of environments extending from veterinary medicine to human drug administrations, and to hobby situations such as fish tanks. The reasons vary, and may address such needs as mimicking a natural intermittent physiological release, allowing for periods of restoration of certain bodily functions between administrations, or adhering to preestablished feeding protocols. One of many examples of situations in which intermittent drug administration is desirable is the administration of somatotropin to swine. Administering the drug in this manner may result in an increase in average daily gain by diminishing the suppression of feed intake, which suppression occurs when the drug is administered at a constant rate and remains at a high level in the bloodstream of the animal. In addition, the pulsed release may increase the therapeutic index of some drugs which would allow for a lower total dose in those cases. Another example is the feeding of fish while one is away on vacation. Other examples abound.

Included in the patent literature relating to pulsatile osmotic pumps is U.S. Pat. No. 4,777,049, issued Oct. 11, 1988 to Magruder, P. R., et al. The pulsatile effect in this patent is achieved by the inclusion of a modulating agent with the beneficial agent to be delivered. The modulating agent is selected on the basis of its solubility in the delivery medium relative to the beneficial agent, and the pulsatile effect results from one of the two falling below its saturation point, causing more of the other to go into solution and thereby be released. The number of pulses one may obtain in this manner is limited, however, and it is difficult to achieve periodic pulses. The system of U.S. Pat. No. 4,723,958, issued Feb. 9, 1989 to Pope, D. G., et al. achieves the pulsatile effect by alternating layers of beneficial agent with layers of inert material. As it is being released, however, the beneficial agent emerges at a slow rate. The system of U.S. Pat. No. 4,842,867, issued Jun. 27, 1989 to Ayer, A. D., et al., is also a layered system, and is best intended for a low number of pulses. Layered systems are also disclosed by Wong, P.S.L., et al., U.S. Pat. No. 4,874,388, issued Oct. 17, 1989; Wong, P.S.L., et al., U.S. Pat. No. 4,957,494, issued Sep. 18, 1990; and Wong, P.S.L., et al., U.S. Pat. No. 5,023,088, issued Jun. 11, 1991.

Devices of the types disclosed in these patents are limited both by their physical configurations and their reliance on the chemicals retained inside them for the pulsatile effect. Control over the intensity and spacing of the pulses which these devices can produce is limited, as is the number of pulses which can be delivered by a single device of reasonable dimensions. Reliability and predictability is also a problem in certain cases.

These and other limitations and disadvantages of known pulsatile delivery systems are addressed by the present invention.

Other literature of possible relevance to this invention are Simpson, B. E., et al., U.S. Pat. No. 4,416,659, issued Nov. 22, 1983; Edwards, S., et al., U.S. Pat. No. 4,867,980, issued Sep. 19, 1989; and LeFevre, R. J., et al., U.S. Pat. No. 4,997,420, issued Mar. 5, 1991. These patents disclose the use of coil springs in slow release capsules. The possible relevance of these patents will be evident from the description which follows.

SUMMARY OF THE INVENTION

The present invention is directed to delivery devices which include a beneficial agent and an activating mechanism in separate compartments separated by a moveable partition, which devices are designed to produce an intermittent or pulsatile release of the beneficial agent by virtue of the structure of the capsule itself rather than the chemical composition or placement of materials contained in the capsule. The intermittent or pulsatile release is produced by forming a band of resilient material that covers the orifice in the wall of the device. The resilient band is sufficiently tight to seal or substantially seal the orifice while at the same time being capable of being stretched in response to pressure generated by the activating mechanism; that is, the orifice remains closed, or at least substantially closed, when the pressure within the device is below a threshold level, and opens as the elastic material stretches when the internal pressure exceeds the threshold. As an example, in the case where the activating mechanism is an osmotic engine, as the capsule absorbs moisture continuously in an aqueous environment the absorbed moisture causes the pressure inside the capsule to rise until the threshold is reached, at which time the band of resilient material stretches to separate sufficiently from the orifice to allow beneficial agent to be released through the orifice until the pressure is sufficiently relieved to cause the band to reseat against the orifice. The cycle is repeated until the beneficial agent is depleted or the capsule is removed from the aqueous environment.

The capsule delivery device of the invention includes a moveable partition which divides the capsule interior into two compartments, a first compartment to contain a beneficial agent and a second compartment to retain an activating mechanism, such as an osmotically active agent. The two compartments vary in volume, with the second compartment expanding or increasing and the first compartment decreasing in volume, as the partition travels within the capsule in response to pressure provided by the activating mechanism, such as, in the case of an osmotically active agent, the fluid flow into and the resulting expansion of the osmotically active agent. The orifice is located in a portion of the capsule wall surrounding the beneficial agent compartment, preferably at a location which remains on the beneficial agent side of the partition at all times during the travel of the partition. In embodiments where the capsule is an elongated structure, the partition moves longitudinally, and the orifice is preferably at or near an end wall.

The pressure build-up in the second compartment due to the action of the activating mechanism is transmitted through the partition to the beneficial agent compartment. In preferred embodiments of the invention, the capsule shell is cylindrical and the fit of the partition is close enough to prevent the passage of fluids around it. Thus, as the partition travels longitudinally within the capsule, the partition maintains sealing contact with the capsule wall during the travel of the partition. This provides the advantage of maintaining the activating mechanism (such as an osmotically active agent, a fluid, or a gas-generating composition, for example) separate from the beneficial agent both when the partition is stationary and when it is in motion. When the pressure in the beneficial agent compartment exceeds the threshold and causes the band of resilient material to stretch, an amount of beneficial agent sufficient to relieve the pressure in the beneficial agent compartment is expelled through the orifice. This release of pressure causes the elastic material to relax and thereby close the orifice.

In further preferred embodiments, the elastic material is not moisture-permeable, nor is any of the wall material surrounding the beneficial agent compartment over the entire range of motion of the partition. The moisture-permeable wall in these embodiments does not extend beyond the osmotic engine compartment, and moisture diffusion into the capsule will thus occur only in the osmotic engine compartment. This provides improved control over the rate at which the beneficial agent is released from the orifice since it provides a more steady rate of moisture imbibition and avoids dilution of the beneficial agent if the beneficial agent itself has moisture-imbibing properties. This also protects beneficial agents that are unstable when exposed to an aqueous environment. In constructions of this type, the functioning of the osmotically active agent is attributable in part to its location on the side of the partition away from the orifice, in conjunction with the fact that only this agent, and not the beneficial agent, is in contact with the moisture-permeable wall. As a result, the selection of the beneficial agent need not be restricted to those species which are not themselves osmotically active, and there is no need to select two agents which differ widely in water-absorptive properties. Nor is there any need to restrict the beneficial agent to those which are stable in aqueous media. Moisture-sensitive beneficial agents, such as certain proteins, peptides and hormones, may thus be delivered without being adversely affected by fluids entering the device.

Further preferred embodiments and their features, and further objects and advantages of the invention, will be apparent from the description which follows.

BRIEF DESCRIPTION OF THE DRAWINGS

FIG. 1 is a side cross-section view of one example of a delivery device in accordance with this invention for pulsatile delivery.

FIG. 2 is an enlarged side cross-section view of the orifice end of the device shown in FIG. 1.

FIG. 3 is an enlarged side cross-section view of an alternative orifice end, according to the present invention.

FIG. 4 is a side cross-section view of a second example of a delivery device according to this invention.

FIG. 5 is an enlarged side cross-section view of the orifice end of the device shown in FIG. 4.

DETAILED DESCRIPTION OF THE INVENTION AND PREFERRED EMBODIMENTS

The pulsatile effect achieved by a device constructed in accordance with this invention, including the length of time between pulses and the sharpness of the pulse, can be controlled by one or more of several parameters. These include the selection of the materials from which the device is constructed, the configuration of the device and its dimensions, and other variables. The degree and manner in which the pulsatile effect can be controlled by these parameters is predictable in some cases, ascertainable by calculation in others, and in still others ascertainable by routine experimentation. These parameters include, for example, the choice of elastic material for the band, the thickness of the band made from the elastic material, the configuration and location of the orifice, and the viscosity and surface tension of the beneficial agent formulation. Additional parameters indirectly affecting the pulsatile effect include the activating mechanism that is utilized; in the case of an osmotic engine, notably the moisture permeability of the wall surrounding the osmotic engine and the absorptive properties of the osmotic engine itself. With appropriate selection and control of these parameters, the interval between pulses may range from minutes to days and may be as short as two or three minutes, although it is typically from about six hours to about 120 days and preferably within the range of from about six hours to about twenty days.

The elastic material itself may be any material which stretches under a pressure differential and then returns to its original configuration once the pressure differential is removed. Preferred elastic materials are elastomers, which in general are synthetic high polymers having properties similar to those of vulcanized rubber, namely the ability to stretch to at least twice their original length and to retract very rapidly to approximately their original length when released. Especially preferred elastomeric materials are those which are nonvulcanized and injection-moldable and are available in food and pharmaceutical grades. Examples include, but are not limited to, styrene-butadiene copolymer, polychloroprene (neoprene), nitrile rubbers (such as acrylonitrile-butadiene rubber), butyl rubber, polyacrylates, polysulfide rubber (Thiokol), polyisoprenes (such as cis-1, 4-polyisoprene), ethylene-propylene terpolymers (such as EPDM), polyepichlorohydrin, polyfluorinated hydrocarbons, silicone rubber, polyurethane rubber, elastomers under the trade name Santoprene® (Monsanto Co.), and the like. Both cross-linked and uncross-linked polymers may be used.

The thickness of the elastic material may vary considerably, and the best thickness for each application will depend on several parameters such as, for example, the size of the device, the desired interval of time between pulses, the viscosity of the material to be delivered, the temperature of use, and the elastic characteristics of the elastic material. The particular thickness can be readily determined by a person of ordinary skill in the art without undue experimentation. In general, the elastic material may be, for example, from at least about 0.005 in (0.013 cm) to about 0.5 in (1.27 cm) in thickness, preferably from at least about 0.010 in (0.025 cm) to about 0.10 in (0.254 cm) in thickness.

For those devices which are elongated capsules, the location of the orifice in preferred embodiments of the invention is at or near the end wall of the device, and the elastic material will completely cover the orifice. In further preferred embodiments, a trough is present in the outer surface of the side wall of the capsule near the first end and encircling the capsule. The orifice is located inside the trough. The trough provides a means for seating and retaining the resilient band, which sits within the trough and covers the orifice.

The resilient band will be sufficiently tight to substantially seal the orifice when the band material is at rest. By "substantially seal" as used herein is meant that the resilient band is sufficiently tight to permit at most only a small flow rate of beneficial agent out of the device when relaxed, relative to the flow rate occurring when the elastic band material is stretched under stress from internal pressure. Thus, the orifice may close entirely, permitting no outward flow at all, when the pressure differential is below a threshold value, or it may close sufficiently to permit a flow rate which is only a fraction of the flow rate when open. While it is possible to measure the threshold pressure differential, it is not necessary to do so, since the pulsing effect can be detected and characterized by measurements of the amount and rate of beneficial agent released.

The activating mechanism which is utilized in the present invention to activate the pulsatile delivery of beneficial agent may be selected from any mechanism which provides a delivery of flow at sufficient pressure to ultimately extend or stretch the resilient band. Such mechanism may be a dynamic system or a static system. Dynamic systems include, but are not limited to, osmotic engines; thermal systems; mechanical systems such as pumps using, for example, rotating mechanisms, pistons or vanes (the Harvard® syringe pump and intravenous pumps being examples) or osmotic action (the ALZET® osmotic pump being an example); flow resulting from vapor pressure of fluid; and flow resulting from chemical or electrochemical reactions such as those that generate gaseous products (for example, the electrolysis of water). Static systems include, but are not limited to, elastomeric systems such as those using an inflated bladder; spring-loaded chambers or pistons; and systems dependent on gravity, such as displacement in height (an intravenous bottle being one example).

While this invention is of broad scope and capable of application to many different types of delivery capsules and agents to be delivered by such capsules, the basic elements of the invention and their functions are most easily understood by examination of certain specific embodiments.

Turning now to the Figures, which are not drawn to scale but are presented for purposes of illustration, FIG. 1 depicts, in cross section, a capsule in accordance with the invention which provides a pulsatile effect by virtue of a resilient material laid over an orifice, which material stretches in response to a buildup of pressure inside the capsule. While the orifice and closure may assume a wide variety of structures which will readily occur to those skilled in the art, one example is shown in FIG. 1 and in magnified view in FIG. 2. The capsule 11 is constructed from a membrane cup 12 of semi-permeable (i.e., moisture-permeable) membrane material and a tube 13 of fluid-impermeable material. Both are cylindrical in shape, bodies of revolution about a longitudinal axis. The capsule 11 contains a partition 17 dividing the capsule interior into a beneficial agent reservoir 14 for retaining a beneficial agent and a compartment 15 (or "osmotic engine") for retaining an osmotically active agent. The partition 17 is a single-piece piston which moves as a unit in the direction indicated by the arrow 16 upon expansion of the osmotically active agent. The partition 17 is initially located at the location at which the fluid-impermeable tube 13 and the membrane cup 12 meet, such that all of the osmotically active agent 15 is contained within the membrane cup prior to expansion, receiving the full benefit of the water absorption while the drug 14 is prevented from being diluted by water absorption.

Capsule 11 also includes a cap 18 at the end of the fluid-impermeable tube 13 distal from the moisture-permeable membrane cup 12. Cap 18 is shown in magnified view in FIG. 2. Cap 18 includes an orifice 19 extending from the portion of the cap that is proximate the beneficial agent compartment 14 and through the side wall of cap 18 at a point near the end wall of the cap, to provide an outlet for the beneficial agent. A rectangular cross-section trough 20 is formed in the outer surface of the cylindrical side wall of cap 18, encircling the capsule 11, with the orifice 19 located inside the trough. Although only one such orifice is shown, the trough 20 may contain two or more such orifices. A band 21 of resilient material is seated inside the trough, encircling the capsule. The band is sufficiently tight to seal the orifice, but capable of being stretched by the force of the moving partition 17 (transmitted through the beneficial agent) to separate sufficiently from the orifice to permit escape of the beneficial agent. Once the force is spent, the band once again seats against the orifice.

An alternate embodiment of the orifice and closure of the present invention is illustrated in FIG. 3, which is an enlarged view of the cap end portion of a capsule substantially similar to capsule 11 but having a cap 28, which cap 28 includes multiple orifices 19 through the side wall of the cap to provide outlets for beneficial agent. Two orifices 19 are shown; however, this number is not controlling, and there may be from one to six or more orifices. A semicircular cross-section trough 30 is formed in the outer surface of the cylindrical side wall of cap 28, with the orifices 19 located inside the trough. An O-ring 32 of resilient material is seated inside trough 30, encircling the capsule. The resilient O-ring functions in the same manner as the resilient band of FIG. 2, as described previously herein.

Another embodiment of the orifice and closure according to the invention is shown in FIG. 4, and in magnified view in FIG. 5. FIG. 4 depicts a drug delivery capsule 71 which, like that of the preceding drawing FIG. 1, is cylindrical in form and symmetrical about its longitudinal axis. The partition 72 of the capsule consists of a primary piston 73 facing the drug reservoir 74 and a secondary piston 75 facing the osmotic engine 76, with a compression coil spring 77 joining the two pistons.

The primary piston 73 has a protruding rib 78 around its circumference. This rib engages a series of circular grooves 79 along the inner wall of the capsule shell 80 in succession, to provide a pulsatile action in addition to that provided by the resilient band over the orifice. The secondary piston 75 does not engage the wall of the capsule shell, but instead is free to move (in the sense that it does not encounter resistance from the wall) in the direction indicated by the arrow 81 in response to expansion of the osmotic engine 76. With continuous imbibition of water by the osmotically active agent in the osmotic engine, the secondary piston 75 advances continuously, compressing the spring 77 until the force exerted by the spring on the primary piston 73 is sufficient to force the protruding rib 78 out of the groove 79 in which it is resting, thereby initiating a delivery pulse. The residual force of the spring then pushes the primary piston further forward until the rib engages the next groove, and the pulse is terminated.

The coil spring 77 shown in FIG. 4 thus acts as a capacitance means. The coil spring may be substituted by any compressible material or linkage which is capable of storing energy upon compression which is later released when the compressive force is removed or overcome. Thus, capacitance means such as a compressible gas or an insert of resilient compressible closed-cell foam, or further substitutes which will readily occur to those skilled in the art, may be used in place of the spring.

The composite partition structure is discussed in greater detail in U.S. Ser. No. 07/837,183, the entire disclosure of which is incorporated herein by reference.

The beneficial agent is released from the capsule through an orifice 91 at the end of the capsule opposite that of the osmotic engine. While the spring 77 provides each pulse with a sharper profile (as indicated by a plot of quantity of agent released vs. time), the profile is rendered even sharper by the use of a resilient closure 92 over the orifice, according to the present invention. Such a closure will be forced open by the force of the spring 77 when the primary piston 73 is in motion, and will return to a closed position by its own resilient force once the protruding rib 78 of the primary piston comes to rest in one of the grooves 79. The closure thus functions as a relief valve or check valve, which not only provides quick opening and closing of the orifice to prevent beneficial agent from seeping or diffusing out between pulses, but also prevents the external medium from diffusing in.

As shown in greater detail in FIG. 5, the portion of the capsule shell 93 which encloses the drug reservoir 74 is closed at the end 94, and the orifice 91 is a small circular passage through the cylindrical side wall of the shell near the end wall. A rectangular cross-section trough 95 is formed in the outer surface of the cylindrical side wall, encircling the shell, with the orifice 91 located inside the trough. Although only one such orifice is shown, the trough 95 may contain two or more such orifices. A band 96 of resilient material is seated inside the trough, encircling the shell. The band is sufficiently tight to seal the orifice, but capable of being stretched by the force of the primary piston 73 (transmitted through the drug) to separate sufficiently from the orifice to permit escape of the drug. Once the force is spent, the band once again seats against the orifice.

While the materials and dimensions at this end of the capsule may vary widely, the following is a list of parameters of a representative structure:

| | |
|---|---|
| outer diameter of shell: | 0.192 in (0.488 cm) |
| shell wall thickness: | 0.031 in (0.079 cm) |
| trough width: | 0.10 in (0.254 cm) |
| trough depth: | 0.013 in (0.033 cm) |
| orifice diameter: | 0.015 in (0.038 cm) |
| band material: | Santoprene ® 281-55 |
| outer diameter of band: | 0.162 in (0.41 cm) |
| band width: | 0.10 in (0.254 cm) |
| band thickness: | 0.0185 in (0.047 cm) |

Further structural and functional parameters of the capsules described above may be varied widely, and appropriate or optimal values and qualities for these parameters will vary with the particular application, such as the nature of the beneficial agent to be delivered, the type of environment into which the delivery is made, and the purpose of and desired protocol for the delivery, including the number, frequency and intensity of the pulses. The design of a system which will produce a selected delivery protocol is well within the routine skill of those experienced in controlled release systems and semi-permeable materials. These parameters are discussed in more detail in U.S. Ser. No. 07/837,183, previously incorporated herein by reference.

While these and other structural parameters of capsules accordance with this invention may vary widely, the following is a list of structural parameters for a representative capsule of the structure shown in FIG. 4:

| | |
|---|---|
| external length of capsule: | 2.0 in (5.08 cm) |
| internal diameter of drug reservoir between grooves: | 0.129 in (0.328 cm) |
| number of grooves: | 42 |
| center-to-center spacing between grooves: | 0.027 in (0.069 cm) |
| depth of each groove: | 0.005 in (0.127 cm) |
| angle of each groove: | 90° |
| primary piston material: | thermoplastic elastomer (Santoprene) |
| diameter of primary piston (exclusive of projecting rib): | 0.130 in (0.33 cm) |
| diameter of primary piston at projecting rib: | 0.137 in (0.35 cm) |
| spring material: | stainless steel |
| spring length: | 0.125 in (0.32 cm) |
| spring diameter: | 0.088 in (0.22 cm) |
| spring wire gauge: | 0.012 in (0.03 cm) |
| spring constant: | 12.7 lbf/in (22.2 N/cm) |
| spring force at maximum compression: | 0.90 lbf (4.0N) |

FIG. 4 further illustrates a feature related to the construction of the osmotic engine compartment of the capsule, which feature is included in preferred embodiments of the osmotic device. As in FIG. 1, the osmotic engine is retained in a semi-permeable membrane cup 85. The cup is surrounded by a close-fitting sleeve 86 made of rigid material and closed at the end. Both the end wall and the cylindrical side wall of the sleeve 86 have holes (not shown) arranged in a regular pattern to permit access of the surrounding medium to the membrane cup 85. The sleeve 86 prevents the membrane cup from bursting or expanding due to the increasing pressure transmitted by the spring 77 as the result of the osmotic imbibition. The sleeve may be constructed of any inert material capable of withstanding the pressure exerted by the spring at its maximum compression without significant distortion. While the composition of the sleeve may be that of a semi-permeable material, in a presently preferred embodiment, the composition is of a material which is substantially impermeable to fluids (except for the holes) One example is Lexan® polycarbonate; other examples will be readily apparent to those skilled in the art.

While dimensions and configurations for the sleeve 86 may vary widely, the following is a list representing one example:

| | |
|---|---|
| length of sleeve: | 0.564 in (1.43 cm) |
| wall thickness adjacent to membrane cup: | 0.0375 in (0.095 cm) |
| number of holes in side wall: | 20 |
| diameter of side wall holes: | 0.0625 in (0.159 cm) |
| number of holes in end wall: | 3 |
| diameter of end wall holes: | 0.050 in (0.127 cm) |

Aside from the qualities of permeability and elasticity, the materials of construction of this capsule and all other capsules in accordance with this invention are not critical and may vary widely, provided that they are inert, capable of maintaining structural integrity and withstanding the stresses encountered during placement of the capsule and its operation in absorbing moisture and delivering the beneficial agent, and either semipermeable or impermeable, depending on the portion of the capsule or capsule wall in which they are used. While fluid-impermeable materials are presently preferred for the portion of the capsule wall surrounding the beneficial agent, it is to be understood that such walls may, in an alternate embodiment, be prepared with fluid-permeable (semipermeable) materials and such is contemplated and encompassed by the present invention.

Preferred moisture-permeable wall materials are cellulosic materials, such as cellulose esters, cellulose ethers and cellulose ester-ethers. These and other suitable materials, as well as materials which may be included as modifiers or additives, are well known to the art. Examples are discussed in U.S. Ser. No. 07/837,183, previously incorporated herein by reference.

The non-fluid-permeable portion of the capsule wall, the partition separating the osmotic engine from the beneficial agent reservoir, and the close-fitting sleeve surrounding the semipermeable membrane may be constructed of any material which is inert, fluid-impermeable, and of sufficient resilience to function effectively for pulsatile delivery. The need for and degree of resilience will vary depending in part on its location in the capsule, and in part on the capsule structure, as illustrated by the differences among the drawings herein. In general, however, typical materials of construction suitable for these parts include polyolefins, condensation polymers, addition polymers, organo-silicon polymers and inorganic polymers. Specific examples are high density polyethylene, high density polypropylene, polystyrene, polycarbonate, polyamides, elastomers in general, chlorinated rubbers, styrene-butadiene rubbers, chloroprene rubbers, silicones, and glass. Several of these materials are elastomers, but will be used with a thickness which does not permit the degree of expansion which the resilient band at the orifice will exhibit under the same pressure differentials.

Delivery capsules in accordance with the present invention for the pulsatile delivery of beneficial agents may be manufactured by a variety of techniques, many of which are described in the literature. In one such technique, the beneficial agent and an osmotically active agent are prepared as solid or semi-solid formulations and pressed into pellets or tablets whose dimensions correspond to the internal dimensions of the respective compartments which they will occupy in the capsule interior. Depending on the nature of the materials used, the two agents and other solid ingredients which may be included with them may be processed prior to the formation of the pellets by such procedures as ballmilling, calendering, stirring or rollmilling to achieve a fine particle size and hence fairly uniform mixtures of each. Once the pellets have been formed, they are placed inside a pre-formed capsule with the partition in between. The capsule may be formed from any of the wall-forming materials disclosed above by the use of a mold, with the materials applied either over the mold or inside the mold, depending on the mold configuration. Where an end cap is a part of the device, the end cap is then placed onto the capsule to close it. The resilient band is placed over the orifice.

In other embodiments of this invention, the beneficial agents are flowable compositions such as liquids, suspension, or slurries, and are poured into the capsule after the osmotically active agent and the partition have been inserted. Still further alternatives may include any of the wide variety of techniques known in the art for forming capsules used in the pharmaceutical industry.

The capsule orifice is also formed by conventional techniques described in the literature. Included among these methods are mechanical drilling, laser drilling, and molding. The capsule will contain at least one such orifice, and in most configurations, one orifice will suffice. However, two or more orifices may be present without departing from the present invention. The dimensions of the orifice in terms of both diameter and length will vary with the type of beneficial agent, the amount of beneficial agent to be delivered at each pulse, and the environment into which it is to be delivered. The considerations involved in determining the optimum dimensions of the orifice for any particular capsule or beneficial agent are the same as those for orifices of capsules of the prior art, and selection of the appropriate dimensions will be readily apparent to those skilled in the art.

The osmotic engine is comprised of an osmotically active agent, which agent may be an osmagent, an osmopolymer or a mixture of the two. Species which fall within the category of osmagent, i.e., the non-volatile species which are soluble in water and create the osmotic gradient driving the osmotic inflow of water, vary widely. Examples are well known in the art and include magnesium sulfate, magnesium chloride, potassium sulfate, sodium chloride, sodium sulfate, lithium sulfate, sodium phosphate, potassium phosphate, d-mannitol, sorbitol, inositol, urea, magnesium succinate, tartaric acid, raffinose, and various monosaccharides, oligosaccharides and polysaccharides such as sucrose, glucose, lactose, fructose, and dextran, as well as mixtures of any of these various species.

Species which fall within the category of osmopolymer are hydrophilic polymers that swell upon contact with water, and these vary widely as well. Osmopolymers may be of plant or animal origin, or synthetic, and examples of osmopolymers are well known in the art. Examples are poly(hydroxy-alkyl methacrylates) with molecular weight of 30,000 to 5,000,000, poly(vinylpyrrolidone) with molecular weight of 10,000 to 360,000, anionic and cationic hydrogels, polyelectrolyte complexes, poly(vinyl alcohol) having low acetate residual, optionally crosslinked with glyoxal, formaldehyde or glutaraldehyde and having a degree of polymerization of 200 to 30,000, a mixture of methyl cellulose, crosslinked agar and carboxymethylcellulose, a mixture of hydroxypropyl methylcellulose and sodium carboxymethylcellulose, polymers of N-vinyl lactams, polyoxyethylene-polyoxypropylene gels, polyoxybutylene-polyethylene block copolymer gels, carob gum, polyacrylic gels, polyester gels, polyurea gels, polyether gels, polyamide gels, polyimide gels, polypeptide gels, polyamino acid gels, polycellulosic gels, Carbopol® acidic carboxy polymers having molecular weights of 250,000 to 4,000,000, Cyanamer® polyacrylamides, crosslinked indene-maleic anhydride polymers, Good-Rite® polyacrylic acids having molecular weights of 80,000 to 200,000, Polyox® polyethylene oxide polymers having molecular weights of 100,000 to 5,000,000, starch graft copolymers, and Aqua-Keeps® acrylate polymer polysaccharides.

While the term "drug" appears throughout this specification, its use has been primarily for purposes of convenience. The present invention applies to the administration of beneficial agents in general, which include any physiologically or pharmacologically active substance. Included among the types of agents which meet this description are biocides, sterilization agents, nutrients, vitamins, food supplements, sex sterilants, fertility inhibitors and fertility promoters. Drug agents include drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autocoid systems, the alimentary and excretory systems, the histamine system and the central nervous system. Suitable agents may be selected from, for example, proteins, enzymes, hormones, polynucleotides, nucleoproteins, polysaccharides, glycoproteins, lipoproteins, polypeptides, steroids, analgesics, local anesthetics, antibiotic agents, anti-inflammatory corticosteroids, ocular drugs and synthetic analogs of these species.

Examples of drugs which may be delivered by devices according to this invention include, but are not limited to, prochlorperazine edisylate, ferrous sulfate, aminocaproic acid, mecaxylamine hydrochloride, procainamide hydrochloride, amphetamine sulfate, methamphetamine hydrochloride, benzphetamine hydrochloride, isoproteronol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, thiethylperazine maleate, anisindone, diphenadione erythrityl tetranitrate, digoxin, isoflurophate, acetazolamide, methazolamide, bendroflumethiazide, chlorpropamide, tolazamide, chlormadinone acetate, phenaglycodol, allopurinol, aluminum aspirin, methotrexate, acetyl sulfisoxazole, erythromycin, hydrocortisone, hydrocorticosterone acetate, cortisone acetate, dexamethasone and its derivatives such as betamethasone, triamcinolone, methyltestosterone, 17-β-estradiol, ethinyl estradiol, ethinyl estradiol 3-methyl ether, pednisolone, 17-β-hydroxyprogesterone acetate, 19-nor-progesterone, norgestrel, norethindrone, norethisterone, norethiederone, progesterone, norgesterone, norethynodrel, aspirin, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chlorpromazine, methyldopa, dihydroxyphenylalanine, theophylline, calcium gluconate, ketoprofen, ibuprofen, cephalexin, erythromycin, haloperidol, zomepirac, ferrous lactate, vincamine, diazepam, phenoxybenzamine, diltiazem, milrinone, capropril, mandol, quanbenz, hydrochlorothiazide, ranitidine, flurbiprofen, fenbufen, fluprofen, tolmetin, alclofenac, mefenamic, flufenamic, difuninal, nimodipine, nitrendipine, nisoldipine, nicardipine, felodipine, lidoflazine, tiapamil, gallopamil, amlodipine, mioflazine, lisinolpril, enalapril, enalaprilat, captopril, ramipril, famotidine, nizatidine, sucralfate, etintidine, tetratolol, minoxidil, chlordiazepoxide, diazepam, amitriptylin, and imipramine. Further examples are proteins and peptides which include, but are not limited to, insulin, colchicine, glucagon, thyroid stimulating hormone, parathyroid and pituitary hormones, calcitonin, renin, prolactin, corticotrophin, thyrotropic hormone, follicle stimulating hormone, chorionic gonadotropin, gonadotropin releasing hormone, bovine somatotropin, porcine somatotropin, oxytocin, vasopressin, GRF, prolactin, somatostatin, lypressin, pancreozymin, luteinizing hormone, LHRH, interferons, interleukins, growth hormones such as human growth hormone, bovine growth hormone and porcine growth hormone, fertility inhibitors such as the prostaglandins, fertility promoters, growth factors, and human pancreas hormone releasing factor, and analogs and derivatives of these compounds.

The beneficial agent can be present in this invention in a wide variety of chemical and physical forms, such as solids, liquids and slurries. On the molecular level, the various forms may include uncharged molecules, molecular complexes, and pharmaceutically acceptable acid addition and base addition salts such as hydrochlorides, hydrobromides, sulfate, laurylate, oleate, and salicylate. For acidic compounds, salts of metals, amines or organic cations can be used. Derivatives such as esters, ethers and amides can be used. An active agent can be used alone or mixed with other active agents.

The pulsatile delivery which is provided by devices in accordance with this invention may be for therapeutic purposes, nutritional purposes, preventive purposes, and a wide variety of situations in general. The environments in which the devices may be used include physiological environments within the body of a human or animal, or aqueous environments such as pools, tanks, reservoirs, and the like serving recreational, industrial, or residential purposes. Animals to whom drugs may be administered using systems of this invention include humans and other mammals and warm-blooded animals in general, avians, reptiles and fishes. Household animals, sport animals, farm animals, laboratory animals and zoo animals are included. The invention is of particular interest for application to humans and household, sport and farm animals, particularly mammals. Prominent examples other than humans are sheep, goats, cattle, horses and pigs. For the administration of beneficial agents to animals, the devices of the present invention may be implanted subcutaneously or interperitoneally wherein aqueous body fluids are available to activate the osmotic engine. Devices of the invention may also be administered to the rumen of ruminant animals, in which embodiment the devices further comprise a density element for maintaining the device in the rumen for extended periods of time of up to 120 days or longer. Density elements are well known in the art of drug delivery devices.

The devices of this invention are also useful in environments outside of physiological or aqueous environments. For example, the devices may be used in intravenous systems (attached to an IV pump or bag or to an IV bottle, for example) for delivering beneficial agents to an animal, primarily to humans. They may also be utilized in blood oxygenators, kidney dialysis and electrophoresis, for example. Additionally, devices of the present invention may be used in the biotechnology area, such as to deliver nutrients or growth regulating compounds to cell cultures. In such instances, activating mechanisms such as mechanical mechanisms are particularly useful.

The pulsatile delivery of beneficial agent from a delivery device in this invention may be activated by forces other than osmosis, which forces may be mechanical, elastomeric, vapor pressure or chemical or electrochemical in nature. For example, a shaft may extend from the partition, and this shaft could be inserted into a syringe on a Harvard syringe pump. The syringe plunger of the pump is attached to the shaft of the partition in such manner that the mechanical force applied by the syringe pump to the syringe plunger would substitute for the osmotic imbibition of water to supply a delivery of flow at sufficient pressure to activate the resilient band at the orifice.

While the resilient material covering the orifice and providing a pulsatile delivery effect according to the present invention is referred to throughout herein as a "band" or an "O-ring", it is understood that the resilient material may in fact take any physical shape or configuration as long as it meets the criteria of being sufficiently tight to substantially seal the orifice when the pressure within the device is below a threshold level while at the same time being capable of being stretched when the internal pressure exceeds the threshold.

The following examples are illustrations of the practice of the invention, and are intended neither to define nor limit the scope of the invention in any manner.

EXAMPLE 1

Preparation of Pulsatile Osmotically Driven Delivery Device

A delivery device of the configuration shown in FIG. 4 is manufactured as follows.

First, an osmotic expandable driving member is prepared by adding 7.6 kg of water and 0.4 kg of polyvinylpyrrolidone to a stainless steel container and mixing the components for 20 hours to obtain a smooth binder solution. Next, 10.0 kg of sodium Carbomer®, a sodium salt of polyacrylic acid polymer, is sized by being forced through a 0.028 in (0.07 cm) mesh screen in a fluid air mill set at 780–800 rpm speed. Next, 15.0 kg of sodium chloride is sized by being forced through a 0.028 in (0.07 cm) mesh screen in a fluid air mill set at 780–800 rpm speed.

The 10 kg of screened polymer and the 15 kg of screened sodium chloride are transferred to the granulator bowl of a fluid bed granulator, and 6.13 kg of binder solution is slowly sprayed onto the polymer and the salt in the granulator. The polymer/salt granules are formed in this manner. These resultant granules are sized through a 16-mesh screen of a Sweco Separator.

The amount of granulation from the above steps is 25.2 kg, and this is transferred to a blender. Then, magnesium stearate, a lubricant, is added in an amount equal to 1% of the total granulation including the lubricant. A total of 0.255 kg of magnesium stearate is added. All ingredients are mixed for three minutes at 10 rpm to produce a homogeneous expandable driving composition.

The composition thus formed is pressed into osmotically active tablets in a tablet press at a pressure of 500 lb to produce a round, flat-faced 50 mg tablet as an expandable driving member.

The semi-permeable second wall section that forms the compartment for the osmotically active tablet is prepared as follows. First, 3.85 kg of cellulose acetate butyrate and 1.15 kg of tributyl citrate are dry blended in a mixer for 5 minutes. This produces a polymer plasticizer blend of 77/23 ratio for the rate-controlling semi-permeable wall. The blend is then placed in an injection mold and molded into a semi-permeable membrane cup of the desired shape with an open end for receiving an expandable driving member and for mating with the forward wall section, whose preparation is as follows.

The forward wall section, which forms the compartment holding the beneficial agent, is prepared by adding 5 kg of polycarbonate (Calibre® 2000 series, Dow Chemical) to a hopper dryer and drying the polymer at 250° F. for 4 hours. The polymer thus dried is fed into the hopper of an injection mold in which the forward, impermeable, wall section is formed in the desired shape, with an open back end for mating with the semi-permeable membrane cup. The forward wall section thus formed is cylindrical, its inside wall having 42 machined triangular grooves along the length of the wall, each groove being 0.005 in (0.013 cm) deep and 0.027 in (0.069 cm) from center to center. The forward wall section also has a circumferential groove on its exterior surface at the anterior end, of rectangular cross section, as shown in FIG. 5. The groove is 0.10 in (0.254 cm) wide and 0.013 in (0.033 cm) deep. In the bottom of this groove, i.e., its cylindrical surface, and centered 0.07 in (0.178 cm) from the posterior side is a 0.015 in (0.038 cm) exit orifice. This orifice is covered by a relief valve band made from medical grade Santoprene® 281–55 or 281–64, a thermoplastic elastomer, the band having an outer diameter of 0.162 in (0.411 cm), a width of 0.10 in (0.254 cm) and a wall thickness of 0.0185 in (0.047 cm). This band is stretched over the first wall section and seated in the groove, laying flush to the outside wall of the first wall section, thereby filling the annular groove and covering the exit orifice.

The close-fitting sleeve surrounding the semi-permeable membrane cup is prepared by adding 5 kg of polycarbonate (Lexan® HP 1, General Electric) to a hopper dryer and drying the polymer at 250° F. for 4 hours. The polymer thus dried is fed into a hopper dryer of an injection molder where a single-cavity hot tip mold is used to injection mold the sleeve in the desired shape, which is 0.564 in (1.43 cm) in length with one open end for mating with the fully assembled delivery device. The internal diameter of the open end is 0.195 in (0.495 cm) and extends 0.164 in (0.417 cm) into the sleeve. At this point, the internal diameter is reduced to 0.160 in (0.406 cm), the outer diameter of the semi-permeable membrane cup. Around the smaller diameter portion of the sleeve are formed five sets of holes equally spaced longitudinally on the sleeve, the diameter of the holes being 0.0625 in (0.159 cm). There are also three holes in the closed end of the sleeve, the diameter of these holes being 0.050 in (0.127 cm).

The elastomeric secondary partition or piston is prepared by injection molding Santoprene® 281–55, a thermoplastic elastomer, into a four-ribbed piston, weighing approximately 31 mg. The piston thus formed is lubricated with silicone medical fluid 1000 cs to facilitate movement of the piston inside the device.

The elastomeric primary piston is prepared in the same manner as the secondary piston. This piston is then fitted with a Buna 25–70 O-ring in one of the end grooves on the piston created by the ribs. This gives the primary piston the dimensions required for it to seat in the triangular grooves in the inner wall of the impermeable forward wall section.

The delivery device is assembled by first charging the subassembly comprising the semi-permeable membrane cup with two of the osmotic tablets. The lubricated secondary piston is then inserted on top of the osmotic tablets, followed by a stainless steel capacitor spring. The spring is 0.125 in (0.32 cm) long, with a diameter of 0.088 in (0.22 cm), a wire gauge of 0.012 in (0.03 cm), a spring constant of 12.71 bf/in (22.2N/cm) and a force at maximum compression of 0.901 bf (4.ON). The primary piston is placed on top of the capacitor spring. Next, the delivery device subassembly comprising the substantially fluid-impermeable forward wall member is filled with 340 mg of beneficial agent formulation at 40° C., wherein the formulation comprised 33.33 weight percent porcine somatotropin, 4.53 weight percent sodium phosphate monobasic, 28.47 weight percent water, 33.0 weight percent glycerol, and 0.67 weight percent Tween® 80. Then, the two subassemblies are joined at their open ends by partially inserting the membrane cup section into the first wall section. Finally, four drops of moisture-cured cyanoacrylate adhesive are dropped onto the remaining exposed surface, and the members are fully inserted and then twisted to form a sealed delivery device.

The system is completed by joining the sealed delivery device described above with the close-fitting sleeve. These two parts are joined by sliding the sleeve over the membrane cup to seat against the end of the forward wall section on the shoulder inside the sleeve. The sleeve is secured to the first wall section with moisture-cured cyanoacrylic adhesive to effect a sealed, fully protected delivery device.

The foregoing is offered primarily for purposes of illustration. It will be readily apparent to those skilled in the art that the materials, dimensions, manufacturing procedures and other parameters of the system may be further modified or substituted in various ways without departing from the spirit and scope of the invention.

What is claimed is:

1. A delivery device for placement in an environment of use for the pulsatile delivery of a beneficial agent to said environment, the device comprising:
   an enclosure, the enclosure defining an orifice therein;
   activating means within said enclosure for generating a pressure within said enclosure;
   a beneficial agent contained within said enclosure; and
   resilient sealing means for sealing said orifice, said resilient means being displaced from a first position sealing said orifice to a second position opening said orifice when said pressure within said enclosure, generated by said activating means, exceeds a predetermined pressure, said resilient means returning to said first position sealing said orifice when said pressure within said enclosure fails below said threshold pressure.

2. A delivery device in accordance with claim 1 wherein said resilient means for sealing said orifice is selected from elastomeric compounds.

3. A delivery device in accordance with claim 1 wherein said resilient means for sealing said orifice is selected from injection-moldable elastomeric compounds.

4. A delivery device in accordance with claim 1 wherein said activating means is selected from the group consisting of an osmotic engine, a thermal system, a mechanical system, a system dependent on vapor pressure of fluid, a system dependent on chemical or electrochemical reactions, an elastomeric system, a spring-loaded chamber or piston, and a system dependent on gravity.

5. A delivery device in accordance with claim 1 wherein said environment of use is an aqueous environment, at least a portion of said enclosure of said device is permeable to moisture, and said activating means includes an osmotic engine, said activating means within said portion of said enclosure permeable to moisture.

6. A delivery device in accordance with claim 5 which further comprises a partition, said partition movable from a first position to a second position within said interior, said partition dividing said interior into a first compartment and a second compartment, said beneficial agent in said first compartment and wherein said activating means includes at least one osmotically active agent in said second compartment, and in which said resilient means for sealing said orifice and said orifice are constructed such that continuous absorption of fluid from said aqueous environment causes said resilient means to be displaced from a first position sealing said orifice to a second position opening said orifice when said pressure within said enclosure, generated by said activating means, exceeds a predetermined pressure, said resilient means returning to said first position sealing said orifice when said pressure within said enclosure falls below said threshold pressure.

7. A delivery device in accordance with claim 1 which further comprises a capacitance means within said enclosure.

8. A delivery device in accordance with claim 1 which further comprises a density element.

9. A device for providing delivery of a beneficial agent in a pulsatile manner to an environment of use, the device comprising:
   an enclosure having first and second ends and an orifice at or near said first end;
   a partition dividing the interior of said enclosure into a first compartment for containing a beneficial agent and a second compartment for containing an activating mechanism, said first and second compartments being adjacent to said first and second ends, respectively, said partition being capable of moving within said enclosure;
   a beneficial agent in said first compartment; and
   a band of resilient material sealing said orifice on the exterior of said enclosure and covering said orifice, said means for resiliently sealing said orifice being sufficiently tight to seal or substantially seal said orifice but capable of being displaced from a first position sealing said orifice to a second position opening said orifice when said pressure within said enclosure, generated by said activating means, exceeds a predetermined pressure, said resilient means returning to said first position sealing said orifice when said pressure within said enclosure falls below said threshold pressure.

10. A method in accordance with claim 9 wherein said means for resiliently sealing said orifice is selected from elastomeric compounds.

11. A method in accordance with claim 9 wherein said means for resiliently sealing said orifice is selected from injection-moldable elastomeric compounds.

12. A method in accordance with claim 9 wherein said activating mechanism is selected from the group consisting of an osmotic engine, a thermal system, a mechanical system, a system dependent on vapor pressure of fluid, a system dependent on chemical or electrochemical reactions, an elastomeric system, a spring-loaded chamber or piston, and a system dependent on gravity.

13. A method in accordance with claim 9 wherein said environment of use is an aqueous environment, at least a portion of said enclosure of said device adjacent to said second end is permeable to moisture, said activating mechanism is an osmotically active agent or a mixture of osmotically active agents, and said activating mechanism is activated by allowing said device to imbibe fluid from said aqueous environment through said moisture-permeable enclosure to activate said osmotically active agent or agents.

14. A method in accordance with claim 9 wherein said delivery device further comprises a capacitance means in said second compartment.

15. A method in accordance with claim 9 wherein said delivery device further comprises a density element.

* * * * *

UNITED STATES PATENT AND TRADEMARK OFFICE
CERTIFICATE OF CORRECTION

PATENT NO. : 5,456,679
DATED : October 10, 1995
INVENTOR(S) : Stephen M. Balaban, James B. Pike, Jonathan P. Smith, Clifton A. Baile It is certified that error appears in the above-identified patent and that said Letters Patent is hereby corrected as shown below:

Column 15, Line 54, "fails" should read --falls--.

Signed and Sealed this

Thirteenth Day of February, 1996

Attest:

BRUCE LEHMAN

*Attesting Officer*     *Commissioner of Patents and Trademarks*